US00PP23153P2

(12) United States Plant Patent
Pieters

(10) Patent No.: US PP23,153 P2
(45) Date of Patent: Oct. 30, 2012

(54) ***CHRYSANTHEMUM* PLANT NAMED 'DARK SAN REMO RUNNER'**

(50) Latin Name: *Chrysanthemum×morifolium*
Varietal Denomination: Dark San Remo Runner

(75) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 0 days.

(21) Appl. No.: 13/066,466

(22) Filed: Apr. 14, 2011

(51) Int. Cl.
*A01H 5/00* (2006.01)

(52) U.S. Cl. ..... Plt./298

(58) Field of Classification Search ..... Plt./298, Plt./293

See application file for complete search history.

*Primary Examiner* — Annette Para

(74) *Attorney, Agent, or Firm* — C. A. Whealy

(57) ABSTRACT

A new and distinct cultivar of *Chrysanthemum* plant named 'Dark San Remo Runner', characterized by its uniform, upright, outwardly spreading and rounded plant habit; moderately vigorous growth habit; freely branching habit; dense and full plant habit; freely flowering habit; large decorative-type inflorescences with red purple-colored ray florets; long flowering period; and excellent garden performance.

2 Drawing Sheets

Botanical designation: *Chrysanthemum×morifolium*.
Cultivar denomination: 'DARK SAN REMO RUNNER'.

CROSS-REFERENCED TO CLOSELY-RELATED APPLICATIONS

Title: *Chrysanthemum* Plant Named 'Bronze San Remo Runner'
Applicant: Luc Remi Pieters
Filed: Concurrently with this application

BACKGROUND OF THE INVENTION

The present invention relates to a new and distinct cultivar of *Chrysanthemum* plant, botanically known as *Chrysanthemum×morifolium* and hereinafter referred to by the name 'Dark San Remo Runner'.

The new *Chrysanthemum* plant is a naturally-occurring whole plant mutation of *Chrysanthemum×morifolium* 'San Remo Runner', not patented. The new *Chrysanthemum* plant was discovered and selected by the Inventor as a flowering plant from within a population of plants of 'San Remo Runner' in a controlled greenhouse environment in Staden-Oostnieuwkerke, Belgium in October, 2007.

Asexual reproduction of the new *Chrysanthemum* plant by vegetative cuttings was first conducted in a controlled greenhouse environment in Staden-Oostnieuwkerke, Belgium in February, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Dark San Remo Runner'. These characteristics in combination distinguish 'Dark San Remo Runner' as a new and distinct *Chrysanthemum* plant:

1. Uniform, upright, outwardly spreading and rounded plant habit; moderately vigorous growth habit.
2. Freely branching habit; dense and full plant habit.
3. Freely flowering habit.
4. Large decorative-type inflorescences with red purple-colored ray florets.
5. Long flowering period.
6. Excellent garden performance.

Plants of the new *Chrysanthemum* differ primarily from the mutation parent, 'San Remo Runner', in ray floret color as plants of 'San Remo Runner' have dark pink-colored ray florets.

Plants of the new *Chrysanthemum* can be compared to plants of *Chrysanthemum×morifolium* 'Tardel', not patented. In side-by-side comparisons conducted in Staden-Oostnieuwkerke, Belgium, plants of the new *Chrysanthemum* differed from plants of 'Tardel' in the following characteristics:

1. Plants of the new *Chrysanthemum* flowered earlier than plants of 'Tardel'.
2. Plants of the new *Chrysanthemum* had decorative type inflorescences whereas plants of 'Tardel' had daisy type inflorescences.
3. Plants of the new *Chrysanthemum* and 'Tardel' differed in ray floret color as plants of 'Tardel' had yellow-colored ray florets.
4. Plants of the new *Chrysanthemum* were not susceptible to Rust pathogens whereas plants of 'Tardel' were susceptible to Rust pathogens.

Plants of the new *Chrysanthemum* can also be compared to plants of *Chrysanthemum×morifolium* 'Bronze San Remo Runner', disclosed in a U.S. Plant Patent application filed concurrently. In side-by-side comparisons conducted in Staden-Oostnieuwkerke, Belgium, plants of the new *Chrysanthemum* differ primarily from plants of 'Bronze San Remo Runner' in ray floret color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Dark San Remo Runner' grown in a container.

The photograph on the second sheet are close-up views of the upper and lower surfaces of typical inflorescences (left) of 'Dark San Remo Runner' and upper and lower surfaces of typical leaves (right) of 'Dark San Remo Runner'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Dark San Remo Runner'.

Parentage: Naturally-occurring whole plant mutation of *Chrysanthemum×morifolium* 'San Remo Runner', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; medium density.

Plant description:

*Appearance*.—Perennial *Chrysanthemum* with decorative type inflorescences; stems upright and outwardly spreading giving a uniformly rounded appearance to the plant; very freely branching habit with about 40 lateral branches developing per plant; pinching enhances lateral branch development; dense and full plant habit; moderately vigorous growth habit.

*Plant height*.—About 37.5 cm.

*Plant width*.—About 66 cm.

*Lateral branches*.—Length: About 20 cm. Diameter: About 4 mm. Internode length: About 2.3 cm. Strength: Strong. Aspect: Lateral branches positioned about 37.5° from the main stem. Texture: Densely pubescent; longitudinally ridged.. Color: Close to 197A tinged with close to 177A to 177B.

*Leaves*.—Arrangement: Alternate, simple. Length: About 4.1 cm. Width: About 2.3 cm. Shape: Roughly ovate, three-lobed. Apex: Acute. Base: Attenuate. Margin: Palmately lobed and coarsely dentate, sinuses between lateral lobes divergent to parallel. Texture, upper surface: Moderately pubescent. Texture, lower surface: Densely pubescent. Venation pattern: Pinnate. Color: Developing leaves, upper surface: Close to N137B to N137C. Developing leaves, lower surface: Close to 147B. Fully expanded leaves, upper surface: Close to 137A to 137B; venation, close to 146B. Fully expanded leaves, lower surface: Close to 147B; venation, close to 146A to 146B. Petiole: Length: About 5 mm. Diameter: About 2 mm. Texture, upper and lower surfaces: Densely pubescent. Color, upper surface: Close to 146A. Color, lower surface: Close to 146B.

Inflorescence description:

*Appearance*.—Decorative inflorescence form; inflorescences borne on terminals above foliar plane; disc and ray florets arranged acropetally on a capitulum.

*Fragrance*.—Faintly fragrant, pungent.

*Flowering response*.—Long flowering period; under natural season conditions, plants flower continuously from mid-September to late October in Belgium.

*Postproduction longevity*.—Inflorescences maintain good color and substance for about three weeks in an outdoor nursery; inflorescences not persistent.

*Quantity of inflorescences*.—About 25 inflorescences develop per lateral branch; about 1,000 inflorescences per plant.

*Inflorescence bud*.—Height: About 9 mm. Diameter: About 8 mm. Shape: Broadly ovate. Color: Close to 138A.

*Inflorescence size*.—Diameter: About 4.2 cm. Depth (height): About 2.5 cm. Disc diameter: About 8 mm. Receptacle diameter: About 4 mm. Receptacle height: About 3 mm. Receptacle color: Close to 145B.

*Ray florets*.—Length: About 2 cm. Width: About 6 mm. Shape: Narrowly obovate to oblong. Apex: Obtuse to emarginate. Base: Cuneate. Margin: Entire. Aspect: About 65° from vertical. Texture, upper and lower surfaces: Smooth, glabrous; longitudinally ridged. Number of ray florets per inflorescence: About 100. Color: When opening, upper surface: Close to 64A; at the base, close to 150C. When opening, lower surface: Close to 64B; at the base, close to 150C. Fully opened, upper surface: Close to 64A; at the base, close to 150C; color does not change with development. Fully opened, lower surface: Close to 70B; at the base, close to 150C; color does not change with development.

*Disc florets*.—Length: About 1.2 cm. Diameter: About 1 mm. Shape: Tubular, filiform; apices narrowly acute. Texture, inner and outer surfaces: Smooth, glabrous. Number of disc florets per inflorescence: About 50 massed at the center of the inflorescence. Color, immature: Close to 187A; at the base, close to 145B. Color, mature: Close to 187A; at the base, close to 145B.

*Phyllaries*.—Number of phyllaries per inflorescence: About 24 arranged in about three whorls. Length: About 6 mm. Width: About 3 mm. Shape: Ovate. Apex: Bluntly acute. Base: Cuneate. Margin: Entire. Texture, upper surface: Smooth, glabrous. Texture, lower surface: Pubescent. Color, upper surface: Close to 143C; margins, close to N199B. Color, lower surface: Close to 138A; margins, close to N199B.

*Peduncles*.—Length, terminal peduncle: About 6.7 cm. Length, fourth peduncle: About 11.1 cm. Diameter:

About 1.7 mm. Aspect: Erect to about 40° from vertical. Strength: Strong. Texture: Densely pubescent. Color: Close to 148B.

*Reproductive organs*.—Androecium: Not observed. Gynoecium: Present only on ray florets. Quantity: One pistil per floret. Pistil length: About 5 mm. Style length: About 4 mm. Style color: Close to N144B. Stigma shape: Cleft, decurrent. Stigma color: Close to 9C. Ovary color: Close to 144C to 144D.

*Seed/fruit*.—Seed and fruit production have not been observed.

Disease/pest resistance: Plants of the new *Chrysanthemum* have been observed to not be susceptible to Rust pathogens. Resistance to pests and other pathogens common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Dark San Remo Runner' as illustrated and described.

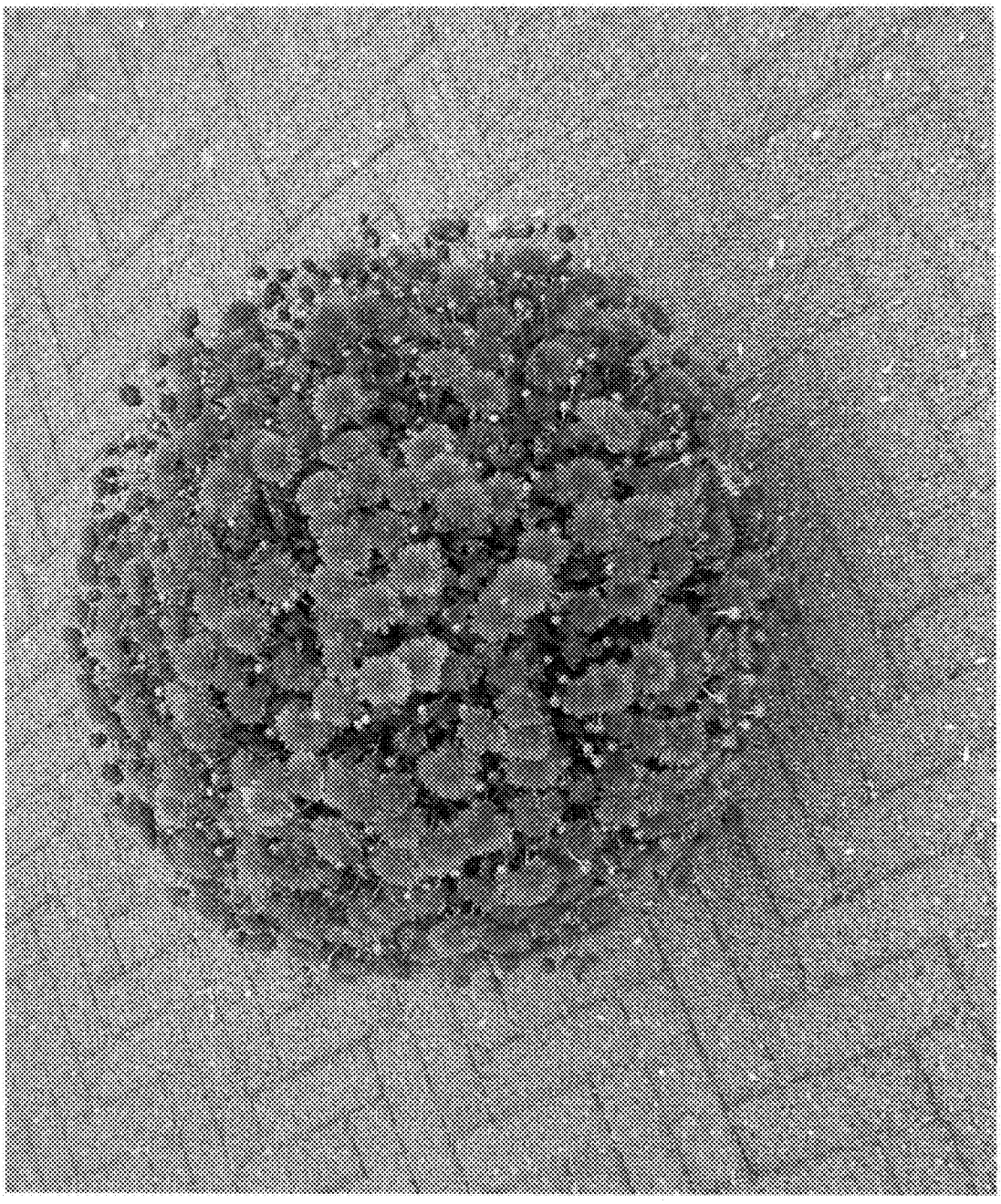

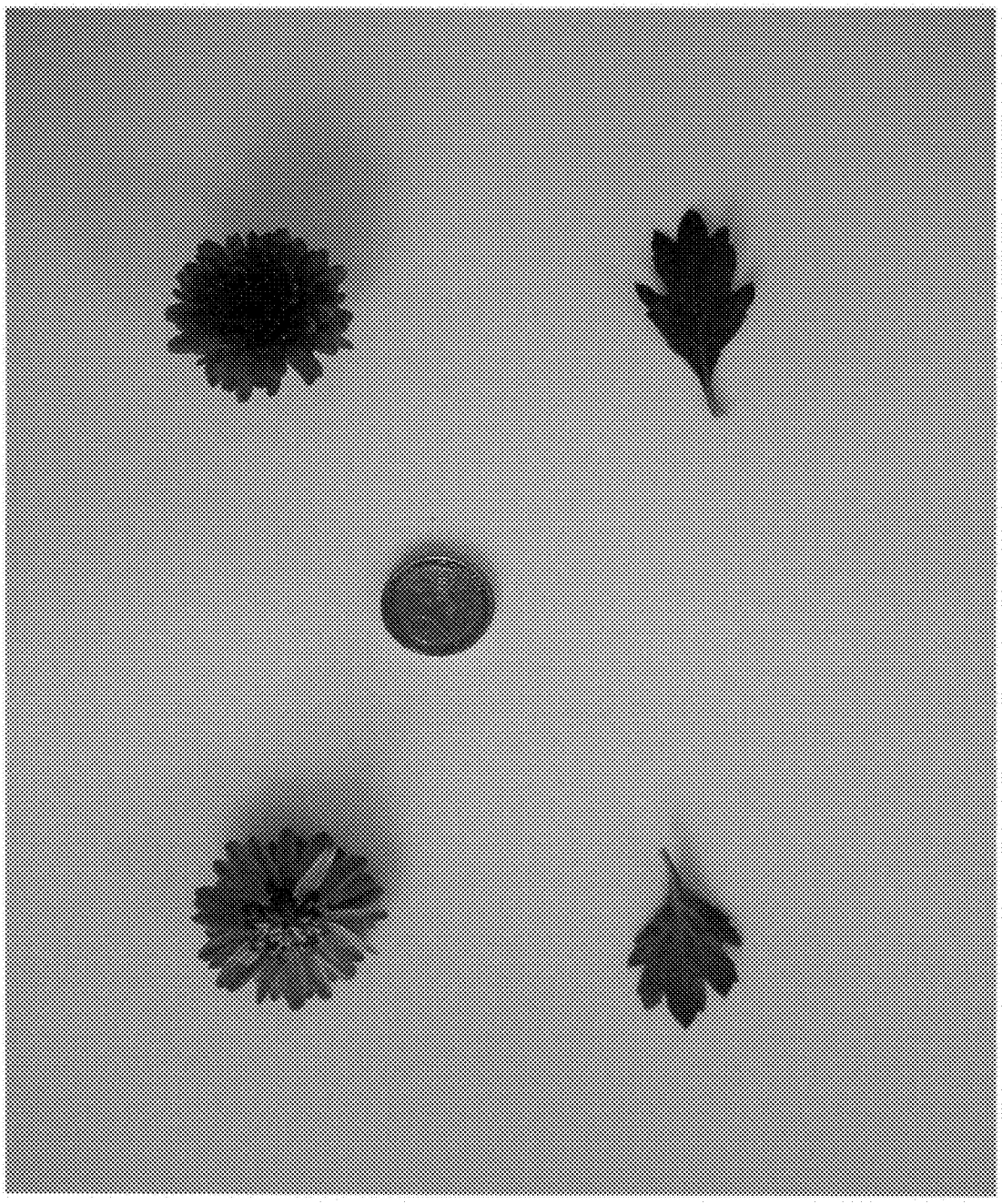

* * * * *